(12) United States Patent
Cornelius et al.

(10) Patent No.: US 8,685,348 B2
(45) Date of Patent: Apr. 1, 2014

(54) NANOWIRE STRUCTURAL ELEMENT

(75) Inventors: Thomas Cornelius, Grenoble (FR);
Wolfgang Ensinger, Munster (DE);
Reinhard Neumann, Dossenhelm (DE);
Markus Rauber, Darmstadt (DE)

(73) Assignee: GSI Helmholtzzentrum fur Schwerionenforschung GmbH, Darmstadt (DE)

( * ) Notice: Subject to any disclaimer, the term of this patent is extended or adjusted under 35 U.S.C. 154(b) by 211 days.

(21) Appl. No.: 12/933,254

(22) PCT Filed: Mar. 12, 2009

(86) PCT No.: PCT/EP2009/001778
§ 371 (c)(1),
(2), (4) Date: May 12, 2011

(87) PCT Pub. No.: WO2009/115228
PCT Pub. Date: Sep. 24, 2009

(65) Prior Publication Data
US 2011/0223412 A1 Sep. 15, 2011

(30) Foreign Application Priority Data

Mar. 20, 2008 (DE) .......................... 10 2008 015 333

(51) Int. Cl.
*B01J 8/00* (2006.01)
(52) U.S. Cl.
USPC ........... 422/603; 422/211; 422/129; 977/762; 977/902
(58) Field of Classification Search
USPC ................... 422/211, 129, 603; 977/762, 902
See application file for complete search history.

(56) References Cited

U.S. PATENT DOCUMENTS

| | | |
|---|---|---|
| 5,449,917 A | 9/1995 | Clements |
| 5,911,863 A | 6/1999 | Vetter et al. |
| 6,328,342 B1 | 12/2001 | Belousov et al. |

(Continued)

FOREIGN PATENT DOCUMENTS

| | | |
|---|---|---|
| DE | 10 2008 015 | 10/2009 |
| EP | 1884578 A1 | 2/2008 |

(Continued)

OTHER PUBLICATIONS

Machine Translation of the reference Rauber, cited in the IDS dated Sep. 17, 2010.*

(Continued)

*Primary Examiner* — Lessanework Seifu
(74) *Attorney, Agent, or Firm* — Reising Ethington PC

(57) ABSTRACT

The invention concerns a nanowire structural element which is suited for implementation in, for example, a microreactor system or microcatalyzer system. For the production of the nanowire structural element, a template based process is used wherein the electrochemical deposition of the nanowires in nanopores is ideally carried out at least until caps are formed and said caps ideally are at least partially merged together. After reinforcing the two cover layers the structured hollow chamber between the two cover layers is cleared by dissolving the template foil and removing the dissolved template material, wherein the two cover layers remain intact. In this manner, a stable sandwich-like nanostructure is constructed with a two-dimensional hollow chamber-like structure in the plane parallel to the cover layers contained on both sides by the cover layers and permeated in a column-like manner with nanowires.

14 Claims, 11 Drawing Sheets

(56) References Cited

U.S. PATENT DOCUMENTS

Figure 6:
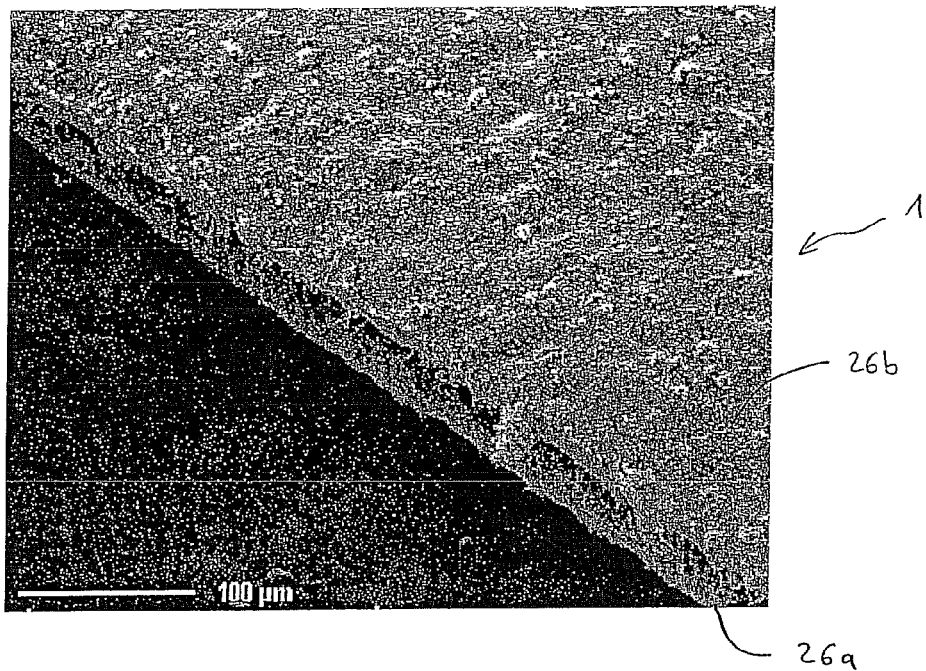

| | | | |
|---|---|---|---|
| 6,383,923 B1 * | 5/2002 | Brown et al. | 438/666 |
| 2005/0230353 A1 | 10/2005 | Danziger | |
| 2006/0134392 A1 | 6/2006 | Hantschel et al. | |

FOREIGN PATENT DOCUMENTS

| | | |
|---|---|---|
| JP | 2004207448 A | 7/2004 |
| WO | WO 2009/115230 | 9/2009 |
| WO | WO 2010/029550 | 3/2010 |

OTHER PUBLICATIONS

Rauber, M.:"Herstellung and Charakterisierung von Edelmetall-Nanodraht-Arrays Diplomarbeit" Aug. 31, 2007 Philipps-Universitat Marburg—GSI XP002547634.

Lindberg M.; Hjort K:"A comprehensive study of ion track enabled high aspect ration microstructures in flexible circuit boards" Microsystem Technologies, Berlin, DE Bd. 10, Date: 2004.

Ursache Andrei; Goldbach James; Russell Thomas; Tuominen Mark: Pulse electrodeposition and eletrochemical quartz crystal microbalance techniques for high perpindicular magneti.

Nielsch, K. et al.: "Uniform Nickel Deposition into Ordered Alumina Pores by Pulsed Electodeposition" Advanced Materials, Bd. 12 Nr. 8, Apr. 4, 2000 Seiten 582-586.

Yi-Kun, Su, et al: Microstructure and Magnetic Properties of Bamboo-like . . . Chemical Physics Letters, Bd. 388, Nr.4-6 Apr. 21, 2004 Seiten 406-418 XP002547633.

Gu, Z. et al:Three Dimensional Electrically Interconnected Nanowire Networks Formed by Diffusion Bonding Langmuir Bd. 23, Nr. 3, Dec. 23, 2006, Seiten 979-982 XP002547983.

Maurer, Florin, et al:"Preferred growth orientation of metallic fcc nanowires under direct and alternating electrodeposition conditions" Nanotechnology 18, pp. 135709 (2007).

Karim, S., et al:"Tuning the Characteristics of Electrochemically Fabricated Gold Nanowires" J.Nanosc.Nanotechnol.8, pp. 5659-5666 (2008).

Karim, S., et al:"Synthesis of gold nanowires with controlled crystallographic characteristics" App. Phys. A 84, pp. 403-407 (2006).

M. Lindeberg, et al "Interconnected Nanowire Clusters in Polyimide for Flexible Circuite and Magnetic Sensing Applications" Sensors and Actuators A, vol. 105, No. 2 150-161, Date: 2003.

Donghai Wang, et al "A General Route to Macroscopic Hierarchical 3D Nanowire Networks" XP-002547982 Angew Chem Int Ed 2004, 43, 6169-6173.

J. Liu, et al "Electrochemical Fabrication of Single-Crystalline and Polycrystalline Aunanowires: the influence of deposition parameters" Inst of physics pub. Nanotech 17 2006.

Japanese Office Action Re: Application No. 2011-500077 Dated: Oct. 18, 2013 Patent Office.

* cited by examiner

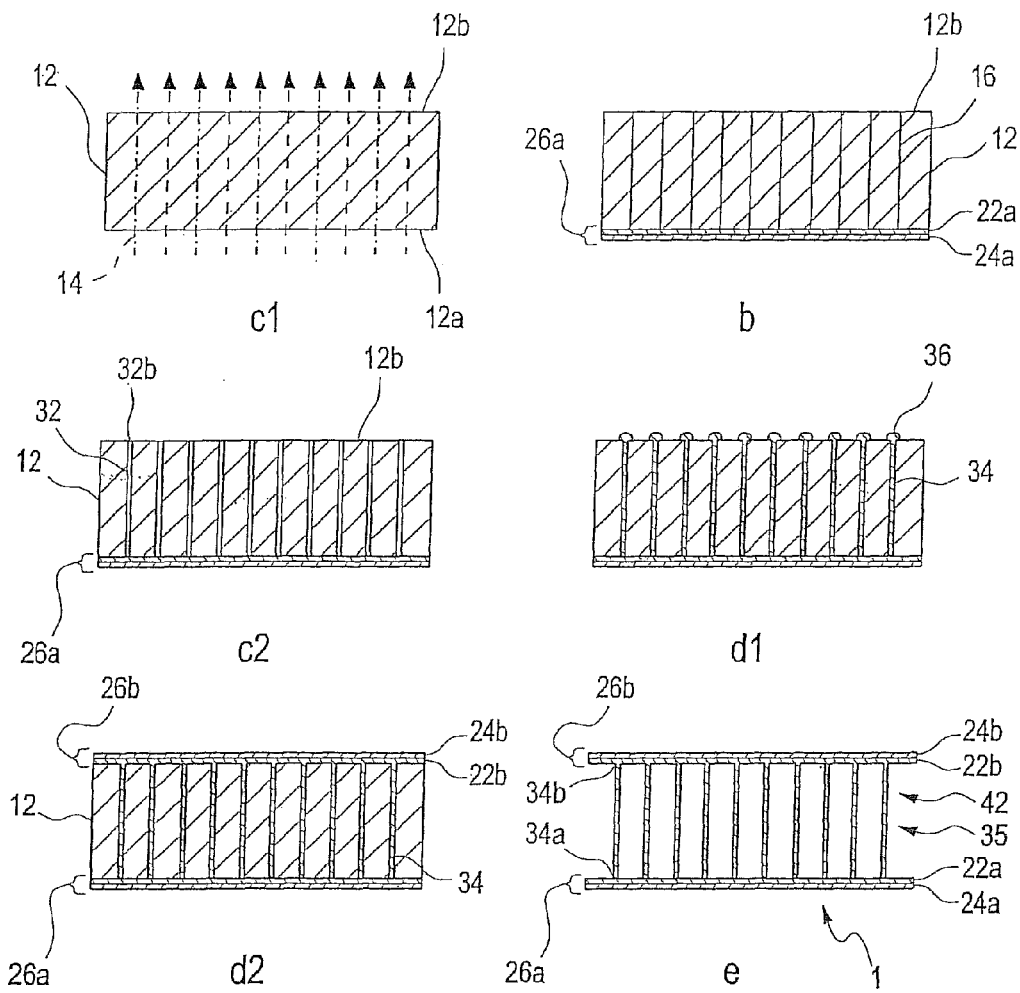
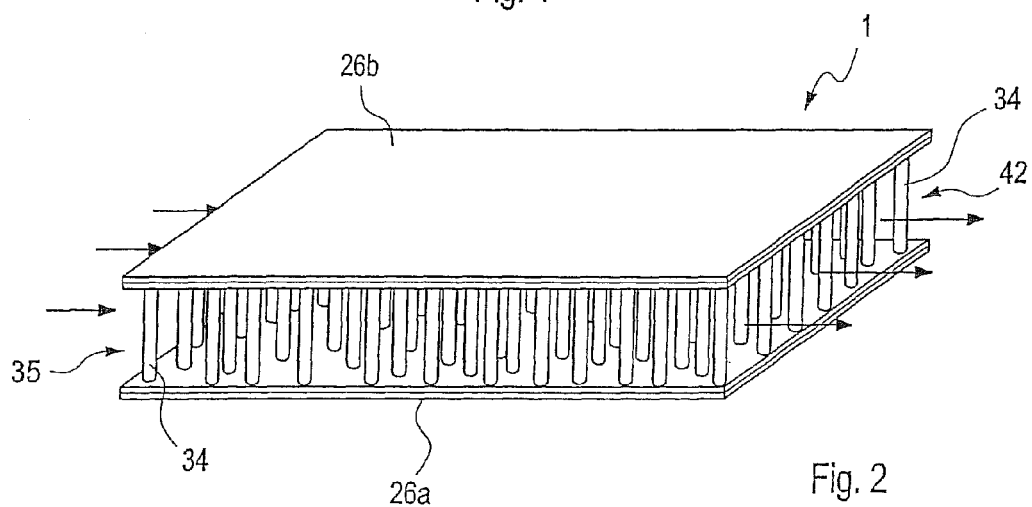

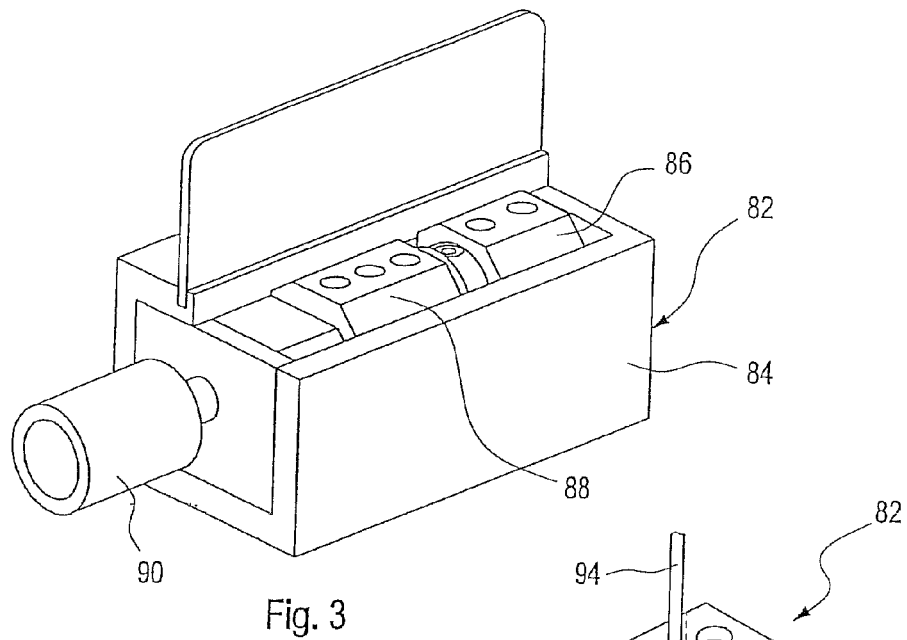
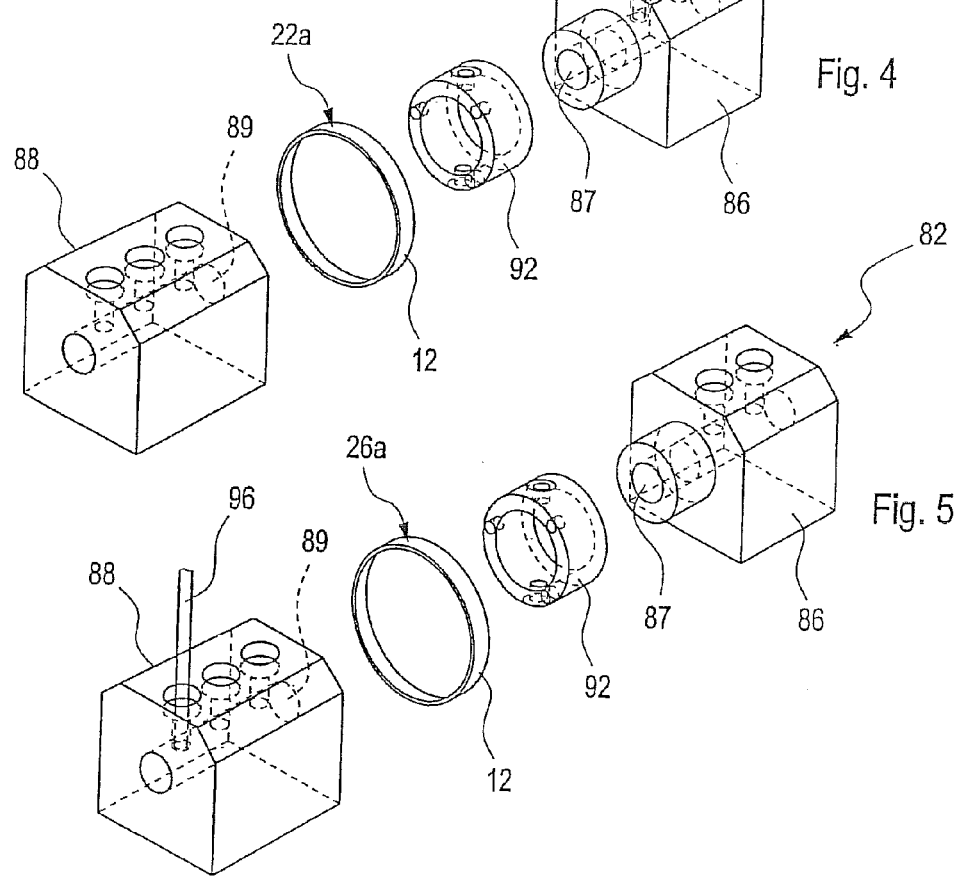

Fig. 19
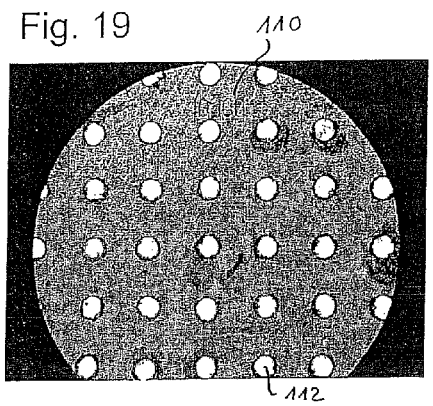
Fig. 20
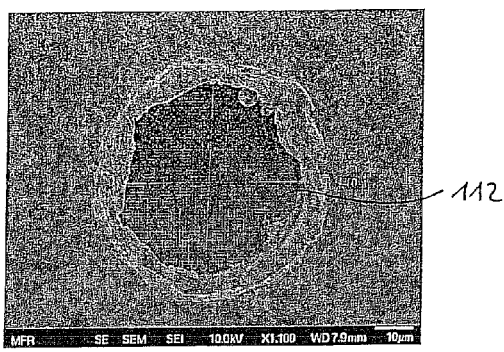
Fig. 21
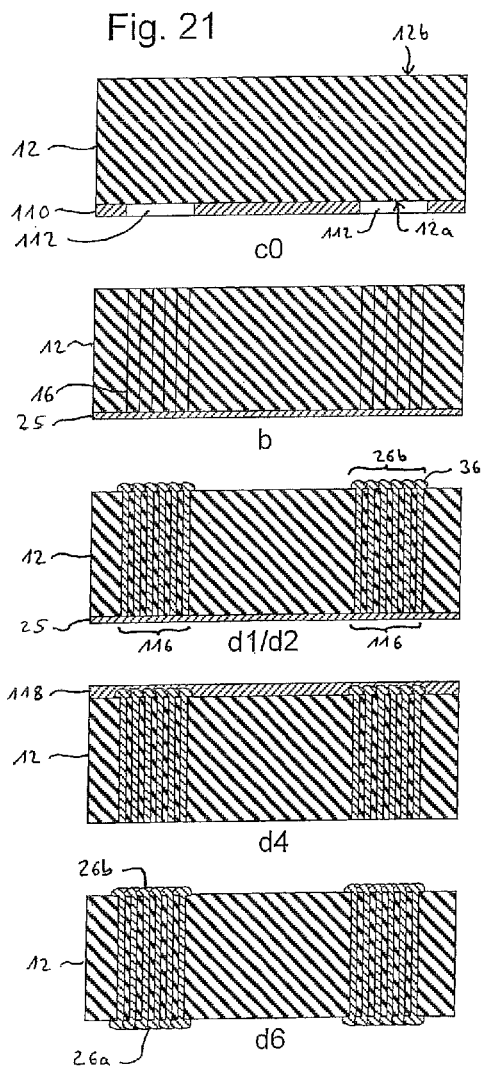
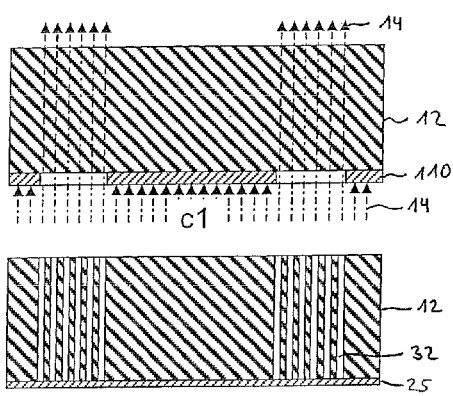

NANOWIRE STRUCTURAL ELEMENT

FIELD OF THE INVENTION

The invention concerns a nanowire structural element, a process for production of said and a micro-reactor system, specifically a microcatalyzer system.

BACKGROUND OF THE INVENTION

In "Chemistry in Microstructured Reactors," Ang. Chem. Int. Ed. 2004, 43, 406-466 [: Applied Chemistry, International Edition], K. Jähnisch et al. have demonstrated the advantages that microstructured components have in chemical reactions and for analytical purposes. This has led to an increase in the importance that such systems have for chemical synthesis and analysis. In comparison to conventional reactors, these microstructures have a large surface area/volume ratio, which has a positive influence on the transference of heat as well as the process of the transportation of matter (see also: O. Wörz et al. "Micro-reactors—A New Efficient Tool for Reactor Development," Chem. Eng. Technol. 2001, 24, 138-142).

Many known reactions have been carried out in microstructure reactors, including many catalytic reactions. For these, it is unimportant whether the reactions are liquid phase, gas phase or gas-liquid phase reactions. In order to take advantage of the potential activity of the catalyzer, the catalytic material is integrated in microstructured systems with various geometric forms. In the simplest case, the reaction material used for the construction of the micro-reactor consists in itself of the catalytically active substance (see also: M. Ficthner, "Microstructured Rhodium Catalysts for the Partial Oxidation of Methane to Syngas under Pressure," Ind. Eng. Chem. Res. 2001, 40, 3475-3483). This means however that the catalytic surface is limited to the walls of the reactor. This disadvantage is partially resolved by means of optimized catalyzer/carrier systems. For the most part, current microstructure reactors contain small particles or powder, which are incorporated in a channel.

Catalyzer filaments, wires and membranes are also used however (see also: G. Veser, "Experimental and Theoretical Investigation of $H_2$ Oxidation in a High-Temperature Catalytic Microreactor," Chem. Eng. Sci. 2001, 56, 1265-1273). Metallic nanostructures, particularly those from transition metals, are known in heterogenic catalysis due to their high ratio of surface area/mass, resulting in lower production costs (see also: R. Narayanan et al. "Catalysis with Transition Metal Nanoparticles in Colloidal Solution: Nanoparticle Shape Dependence and Stability," J. Chem. Phys. B, 2005, 109, 12633-12676).

Originally, research was concentrated on the examination of isotropic metal particles, and as a result, their catalytic characteristics have been studied at length. At present, however, many one-dimensional nanostructures have been analyzed regarding their use in heterogenic catalysis. The stabilization of these is a major problem. The incorporation of nanostructures on a carrier or storage of them in porous matter such as, e.g. Nafion is known from Z. Chen et al. "Supportless Pt and PtPd Nanotubes as Electrocatalysts for Oxygen-Reduction Reactions," Ang. Chem. 2007, 119, p. 4138-4141, which leads however directly to a decrease in the utilizable catalyzer surface area. Furthermore, it must be noted that the catalytic activity is dependent on the distribution of the catalyzer material due to the diffusion processes. Accordingly, the nanoparticles significantly increase the surface area/volume ratio, but long-term stability of such reactors is relatively limited due to the following:

1. Loss of contact between nanoparticles due to corrosion of the carrier.
2. Dissolving and renewed deposition or Ostwald ripening.
3. Aggregation of the nanoparticles in order to minimize the surface energy.
4. Dissolving of the nanoparticles and migration of the dissolvable ions.

Parallel wire and tube structures have already been used as glucose sensors (J. H. Yuan et al., "Highly Ordered Platinum-Nanotubule Arrays for Amperometric Glucose Sensing," Adv. Funct. Mater. 2005, 15, 803), as electrocatalysts, for example, in alcohol oxidation (H. Wang et al., "Pd Nanowire Arrays as Electrocatalysts for Ethanol Electrooxidation," Electrochem. Commun. 2007, 9, 1212-1216) and for hydrogen peroxide reduction (H. M. Zhang et al., "Novel Electrocatalytic Activity in Layered Ni—Cu Nanowire Arrays," Chem. Commun. 2003, 3022). In these cases however, the nanostructures are freestanding, such that the arrangement is open and instable. Nielsch et al. have reported in "Uniform Nickel Deposition into Ordered Alumina Pores by Pulsed Electrodeposition," Adv. Mater. 2000, 12, 582-586, that pulsed deposition is used for deposition of thin metallic foils.

All in all, there is still a great deal of potential for innovation in the field of nanotechnology.

GENERAL DESCRIPTION OF THE INVENTION

The invention has the object of providing a novel nanowire structural element which may be used in a variety of manners.

A further object of the invention is to provide a process wherein the production of a nanowire structural element having a hollow chamber-like structure is possible.

A further object of the invention is to provide a nanowire structural element having a hollow chamber-like structure with a large specific surface area and which is suited for use as a catalytic element.

The object of the invention is achieved by means of the object of the independent claims. Advantageous embodiments of the invention are defined in the dependent claims.

A process is provided for the production of a nanowire structural element which contains a nanowire array located between two cover layers such that a hollow chamber-like structure is created containing nanowires in a column-like formation. A so-called template based process is used as follows. The hollow chamber-like structure may also be envisioned as a chamber that may be open at one or more edges.

In a first process step (a), first, a dielectric template foil is created. Depending on which process is used for creating the nano-pores, the template foil is, for example, conventional synthetic foil, particularly a polymer foil, but said may also be a glass or mica foil, or an aluminum foil.

In a process step (b) a first electroconductive cover layer encompassing the surface is applied to a first side of the template foil, ideally a metal layer. Ideally, a thing metal layer, e.g. gold is sputtered onto said and subsequently said gold layer is reinforced electrochemically, with copper, for example. This has the advantage that, firstly, a relatively thin layer can be sputtered on. The first electroconductive cover layer has a double function: on one hand, it serves as a cathode for the subsequent electrochemical deposition procedure and on the other hand, later functions as a stable sealed cover layer for the nanowire structural element to be created, i.e. it remains as an integral component of the nanowire structural element to be created, and is not subsequently removed from said.

In a process step (c) numerous nanopores are created in the template foil, which fully penetrate the template foil at a right angle. Regarding the steps (b) and (c), there is no specific order implied by the letters. In regard to this, various alternatives to the order of the processes are possible, which can be derived from the following description.

In a subsequent partial step (d1), starting at the inner side of the first cover layer, nanowires are grown within the template foil by means of electrochemical deposition, i.e. the nanopores are filled from the first cover layer by means of electrochemical deposition, wherein the nanowires develop in the nanopores. For this, the coated dielectric foil penetrated with pores and which has an electroconductive coating on one side, is placed in an electrochemical deposition device, wherein the first cover layer serves as a cathode for the electrochemical deposition procedure of the nanowires. By means of electrochemical deposition of metallic ions, the nanowires are then grown in the nanopores, wherein the nanowires grow from metal within the nanopores, in particular, developing directly on the first cover layer, and are thereby firmly joined to the first cover layer by reason of being grow together as integrally formed elements.

A process of this sort for the creation of nanowires is basically known, and has been demonstrated, for example, in the "Controlled Fabrication of Poly- and Single-Crystalline Bismuth Nanowires" by T. W. Cornelius et al., Nanotechnology 2005, 16, p. 246-249; and in the dissertation by Thomas Walter Cornelius, GSI, 2006; Florian Maurer, GSI, 2007, as well as by Shafqat Karim, GSI, 2007, which is hereby incorporated as a reference.

In these processes, however, only single nanowires are created. In contrast to this, in the present invention a freestanding structural element is produced, wherein the first cover layer is obtained and remains connected to the nanowires, and additionally, in a partial step (d2) a second electroconductive cover layer coating the entire surface is applied to the opposite side of the template foil, which is also an integral component of the nanowire structural element to be created.

The first and second cover layers are integrally joined to the nanowires and cannot be removed later.

Accordingly, the nanowires, in the form of a column array, connect the two cover layers to each other. At this point in the process, directly after the creation of the second cover layer the template foil is still present sandwiched between the two cover layers, as both cover layers are applied directly to the template foil. At this point in the process, the template foil is penetrated by the nanowires, in the same manner as with concrete reinforcement.

When the sandwich-like arrangement consisting of the two cover layers and the template foil penetrated by a large quantity of nanowires has been established to the degree that both cover layers are of sufficient thickness and are thereby stable, the template foil, in a step (e), between the two cover layers, is dissolved, specifically by a chemical process, thereby forming a hollow chamber between the two cover layers, while the nanowires remain intact. If the template foil is a synthetic foil, said can, for example, be removed using a solvent. Other foils, such as glass and mica, are dissolved, for example, using hydrofluoric acid (HF). To dissolve aluminum oxide, diluted bases such as NaOH are sufficient. The template foil is reduced to such small components in the dissolving process that said components can be removed from the hollow chamber permeated with nanowires between the two cover layers without damaging the cover layers or the nanowires.

After the template foil has been fully removed, a structurally stable, hollow component remains, in which the two cover layers are connected by numerous nanowires, and are separated from and parallel to each other. Thereby, the first end of each respective nanowire is integrally connected to the first cover layer, and the respective second end is integrally connected to the second cover layer. Accordingly, as a result of the removal of the template foil, a structured hollow chamber is formed between the two cover layers, wherein the hollow chamber is contained on each side by the cover layers, and penetrated at a right angle to the two cover layers by parallel nanowires. The spaces between the nanowires and between the two cover layers are interconnected in the plane of the two cover layers in such a manner that in the plane of the cover layers, a two dimensional open celled hollow chamber-like structure is defined. In other words, a stable, freestanding nanowire structural element is constructed, which consists of the two closed cover layers and the column-like nanowire array contained in a sandwich-like manner between the cover layers and connected to said cover layers.

This nanowire structural element having a nanowire array enclosed at both surfaces, or respectively, a layered hollow chamber-like structure permeated with a nanowire array, is suited in an ideal manner for use as, for example, a microreactor component for heterogenic catalysis. Furthermore, the nanowire structural element remains stable over a long period of time, as the nanowires are firmly anchored, and do not lie, for example, loosely in microchannels.

In order to obtain a stable connection between the nanowire array and the second cover layer, the electrochemical deposition procedure is carried out at least until caps have been developed on the nanowires at the second side of the template foil. In order to create the second cover layer, furthermore, two particular possibilities are suggested in the following: The electrochemical deposition procedure is continued after the complete filling of the nanopores, wherein caps are generated on the nanowires on the second side of the template foil. In the course of continuation of the electrochemical deposition procedure, the caps grow together to form a coating covering the surface, and this surface covering layer increases in thickness when the deposition period is increased. Accordingly, one can continue the electrochemical deposition wherein the nanowires are generated for as long as necessary until the second cover layer has developed to the point where it forms a sufficiently thick, stable, surface covering layer. In this manner, the nanowires and the entire second cover layer form a unitary integrally formed complete structure consisting of electrochemically depositioned matter. For this, the partial steps (d1) and (d2) are carried out using the same electrochemical deposition procedure with the same electroconductive material.

Alternatively, the electrochemical deposition procedure according to partial step (d1) for the generation of the nanowires is carried out until caps form on the nanowires of the second side of the template foil, and said caps grow together at least in part, but a second stable cover layer is not yet generated, and then arrested. The completion of the second cover layer is obtained thereby in a separate second deposition procedure, wherein a surface covering additional layer is depositioned on the partially merged caps, such that the stable second cover layer is created from the second layer by the partially merged caps and the surface covering additional layer. The, at least partially, merged caps form thereby a first partial layer of the second cover layer, and the additional layer forms a second partial layer of the second cover layer. The separate deposition can also be an electrochemical deposition, but can also be a PVD process, such as, for example, an evaporation process or a sputtering process. Even when the separate deposition procedure is an electrochemical deposition, a different material may be used for the second partial layer than that used for the nanowires and the caps. It has been shown to be particularly beneficial when the nanowires and the caps are generated using a pulsed electrochemical deposition procedure, and the second partial cover is created using a direct current process for the electrochemical deposition. As an example, the nanowires and the caps are created from platinum using a reversed pulse deposition and the second partial layer is created from copper using direct current deposition. By this means, the deposition period and the material costs can be reduced.

Accordingly, the second cover layer is either partially or fully formed of an electroconductive material by means of electrochemical deposition according to partial step (d2), ideally of metal, on the second side of the template foil, such that the second cover layer is integrally joined to the nanowires.

At least the nanowires and the, at least partially, merged caps are accordingly depositioned preferably through pulsation. The pulsed deposition has at least the following alternatives:

1) The deposition is carried out using pulsed deposition, i.e. deposition pulses alternating with deposition free diffusion periods.
2) The deposition is carried out by means of reversed pulse deposition, i.e. deposition pulses alternating with anodic counter pulses.

Both alternatives have the advantage that in the breaks between the deposition pulses, ions in the electrolyte solution can re-diffuse in the nanopores, which leads to a uniform development of the nanowires and the layer of caps which develops therefrom.

The first cover layer can be applied as an integral unit by means of a coating process such as, for example PVD, vaporization or sputtering. Ideally, the first cover layer is however generated at least in two layers, wherein the first partial layer is depositioned by means of PVD, e.g. sputtering or vaporization and said first partial layer is then reinforced, as the case may be, by means of electrochemical deposition, with a second partial layer of another material such as copper on gold.

Currently, two basic known processes for creating nanopores in the template foil are under consideration: firstly, ion radiation induced etching and secondly, anodizing of aluminum foil.

Reference is made regarding the production of nanopore arrays in anodic aluminum oxide to A. P. Li et al., "Hexagonal Pore Arrays with a 50-420 nm Interpore Distance Formed by Self-Organization in Anodic Alumina," Journal of Applied Physics, 84-11, 1998, p. 6023-6026, and a review article by J. W. Diggle, Thomas C. Downie, And C. W. Goulding; p. 365-405 DOI: 10.1021/cr60259a005, which are hereby incorporated as references. Anodic aluminum oxide templates have the characteristic, in particular, that the nanopores are arranged in a regular hexagonal pattern.

With modification of etching properties, induced by ion radiation, a stochastic distribution of the nanopores is obtained. The production of ion track etched templates consists of the generation of nanopores in the following partial steps:

First, a commercially available synthetic foil, e.g. a polymer foil, is irradiated (c1) with high-energy radiation, in particular with a highly energetic ion radiation, such as is available, for example, in the accelerator facility of the Gesellschaft für Schwerionenforschung mbH [: Center for Heavy Ion Research] in Darmstadt. As a result of the irradiation a large number of latent tracks cover the template foil. The tracks thereby indicate that the polymer structure of the foil is corrupted along the trajectory of each irradiation ion. In the un-etched state, these tracks are referred to as "latent."

They are then later enlarged to visible tracks by means of an etching process, creating the nanopores (c2).

Ideally, the ion irradiation is first carried out and then, before etching, the first cover layer is applied. Once the first cover layer is applied to the template foil, the nanopores are etched from the latent ion-induced tracks. In particular thereby, the electroconductive metallic layer is applied to the template foil, and said is electrochemically reinforced, before the latent ion tracks are subjected to the chemical etching process. In this manner, the possibility of deposition of material from the first cover layer in the pores is avoided. By this means, it is possible to obtain an improved mechanical stability of the generated nanowire structural element. Furthermore, the pores are strictly cylindrical and do not taper at either end.

The result of the production process described above is accordingly a nanowire structural element with a hollow chamber-like structure which consists of an array of numerous nanowires arranged next to each other and two parallel, separated, closed surface cover layers, from which the template foil is removed. The two cover layers are integral components of the nanowire structural element and are not separated from the nanowires, but rather remain firmly integrally joined to the nanowires, and more precisely are integrally joined to each other by means of the electrochemical deposition procedure at the atomic/molecular level.

Accordingly, the nanowires extend perpendicularly between the two cover layers and the nanowires are integrally joined with their first ends to the first cover layer and with their second ends to the second cover layer such that the nanowires firmly connect the two cover layers to each other, and define a spacing between the two cover layers like an array of columns. In this manner, a stable sandwich-like nanostructure is formed with a two sided hollow chamber-like structure contained by the cover layers and permeated with the numerous columns of nanowires running through said.

Furthermore, the nanowires themselves are separated such that there are interconnected open spaces between the nanowires. The hollow chamber-like structure is open celled on the two-dimensional plane parallel to the tow cover layers, such that between the two cover layers a fluid can be introduced in the two-dimensional open cell hollow chamber-like structure in order to interact with the cylindrical surfaces of the nanowires forming a large surface area.

By means of the production process, there are however further certain structural properties of the constructed nanowire structural element. Because the nanowires are generated from electrochemical deposition materials, they can have a specific crystal structure which, for example, can be examined by means of X-ray diffraction.

Furthermore, the nanowires are directly, integrally joined at both ends to the respective cover layers due to the electrochemical deposition. As a result of the electrochemical deposition of the nanowires being carried out at least until the caps are formed and where applicable, until they have merged, the nanowires, and at least a part of the second cover layer form an integral unit. This too can be structurally proven, particularly if the nano wires form an integrally formed unit with the caps, and said are at least partially merged together. If the deposition procedure wherein the nanowires are created, after the merging of the caps has been completed and thereby the first partial layer of the second cover layer is formed and a deposition is made of a second partial layer in which the caps have merged in a separate step with modified process parameters, then this can also be structurally provable. This does not only apply to when the cover layer consists of two partial layers of different material.

The diameter of the nanowires is ideally less than or equal to 2000 nm, and particularly preferable is less than or equal to 500 nm, or respectively less than or equal to 100 nm. Currently, diameters of as little as 10 nm or even less appear to be possible to produce.

A larger aspect ratio allows for the production of a larger active surface area of the nanowire structural element. The aspect ratio of the nanowires is therefore ideally greater than or equal to 1:50, particularly preferred is greater than or equal to 1:100.

The distance between the two cover layers, or respectively, the length of the nanowires is determined by the thickness of the template foil, and is ideally less than or equal to 200 µm, particularly preferred is less than or equal to 50 µm.

The surface density of the number of nanowires is equally a measure for the active surface area and is ideally greater than or equal to $n/F=10^7$ cm$^{-2}$, particularly preferred is greater than or equal to $n/F=10^8$ cm$^{-2}$.

As a specific size for the active surface area of the nanowire structural element, the geometric specific surface of the nanowires per area of the nanostructure structure element and per length of the nanowires may be used. Accordingly, this geometrically specific surface area $A_v$ is:

$$A_v = \pi D \cdot \frac{n}{F},$$

Wherein D is the average diameter of the nanowire and n/F is the surface density of the nanowires.

The geometrically specific surface area $A_v$ should be at least 1 mm$^2$/(cm$^2$ µm); larger values however are preferred, specifically where $A_v$ is greater than or equal to 5 mm$^2$/(cm$^2$ µm), greater than or equal to 20 mm$^2$/(cm$^2$ µm) or even greater than or equal to 100 mm$^2$/(cm$^2$ µm). Where applicable, values of up to 1000 mm$^2$/(cm$^2$ µm) may even be obtained.

In the production of the nanowires with the reversed pulse process, the nanowires have a distinct <100> texture, or respectively, a crystalline structure. With certain metals such as, for example, gold, it may be advantageous to create the smallest crystallite possible. For this a crystallite size of less than or equal 4 nm is preferred, wherein in general an average crystallite size of less than or equal to 10 nm may be advantageous.

Due to the crystalline texture, the actual size of the surface area is larger than the geometrically specific surface area $A_v$, which is based on the smooth cylindrical surface area, ideally by a factor of around 4-5.

According to a special embodiment of the invention, very small nanowire structural elements can be produced as well. For this, the template foil is irradiated through a mask with one or more openings such that the latent tracks are only generated in the region of the openings in the mask. In this manner, islands of latent tracks are created. After the etching and application of a first cathode layer on the first side of the template foil, a deposition of the nanowires to the nanopores and the caps to the second side of the template foil is carried out until caps on the second side of the template foil merge together to form islands. Subsequently, an electroconductive cap bridging layer is depositioned to the islands of merged caps thus connecting the islands with each other. This layer serves later as a second cathode layer. After this second cathode layer has been created, the first cathode layer is removed and the electrochemical deposition is continued in the opposite direction, wherein caps are now formed on the nanowires on the first side of the template foil. This deposition procedure is also carried out until the caps merge together in islands. Subsequently, the second cathode layer is removed and the template foil is dissolved. In this manner, numerous island-like nanowire structural elements are created with cover layers on both sides made of merged caps. These island-like nanowire structural elements are very small, e.g. having a diameter of a few micrometers to a few tens of micrometers, and if applicable a few hundred micrometers and are therefore denoted here as microelements.

It is even possible to design components with numerous island-like microelements. For this the second cathode layer is not removed, or one or more cover layers are applied before the template foil is dissolved. The newly applied cover layer(s) may be electroconductive or even electrically insulating. The size and distribution of the islands is predetermined by the openings in the irradiation mask. Accordingly, it is possible to produce a component consisting of numerous predetermined microelements distributed in an island-like manner on a substrate layer, wherein the island-like microelements are distributed on the substrate layer in a pattern predetermined by the radiation mask and which are integrally joined to the substrate layer. The substrate layer specifically, can be either electroconductive or electrically isolating, such that the microelements are either connected with each other electrically or insulated from each other.

A particularly preferred field of application for the nanowire structural elements produced according to the invention is heterogenic catalysis. This means one or more components serve as catalytic components, particularly for microcatalyzers. For this, it is advantageous to extend a cover layer on one or more of the faces over the edge and allow it to merge with the other cover layer, i.e. the respective edge is integrally connected to the nanowire structural element. It is particularly simple to first close all of the edges and then slice off, for example, two opposite edges of the nanowire structural element at right angles to the cover layers.

A microcatalyzer ideally contains a microstructured channel system with a fluid intake and a fluid discharge and at least one nanowire structural element as a catalyzer element between the fluid intake and the fluid discharge, in order that fluid may be introduced by means of the fluid intake to the hollow chamber-like structure between the two cover layers, fed through the spaces between the nanowires and then removed by means of the discharge from the hollow chamber-like structure. In this manner, the two-dimensional open cell hollow chamber-like structure of the nanowire structural element is formed between the two cover layers of the catalytic reaction volumes and the cylindrical surfaces of the nanowire form the catalytically active surface area which interacts with the fluid within the hollow chamber-like structure. Ideally, due to deposition, the nanowires are formed significantly of for example, platinum, in order that the catalytic element is a fully catalytic element.

In the following, the invention will be explained in detail using the embodiment examples and in reference to the illustrations, wherein identical and similar elements have the same reference symbols in part and the characteristics of different embodiments, particularly the procedures with and without radiation masks, can be combined with each other.

SHORT DESCRIPTION OF THE ILLUSTRATIONS

They show:

FIG. 1 An overview of the production of a nanowire structural element; (c1) bombardment with ions, (b) application of an electroconductive layer, (c2) etching of the ion tracks, (d1) deposition of the nanowires and cap development, (d2) deposition of a second metallic layer, (e) dissolving of the template.

FIG. 2 A three-dimensional schematic presentation of the nanowire structural element according to the invention.

FIG. 3 A three-dimensional presentation of the deposition device used for electrochemical deposition.

FIG. 4 A three-dimensional transparent exploded view of the deposition device for the deposition of the first cover layer.

FIG. 5 A three-dimensional transparent exploded view of the deposition device for the deposition of the nanowires and the second cover layer.

FIG. 6 A scanning electron microscope (SEM) image of a nanowire structural element according to the invention.

Figure 7:
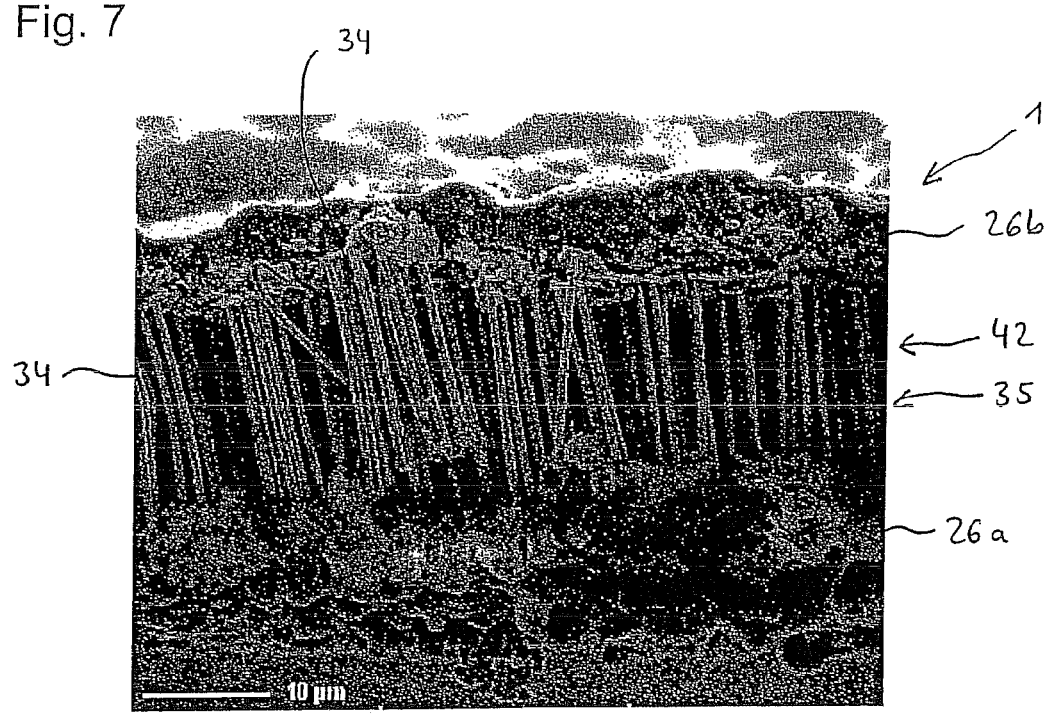

FIG. 7 An enlarged side view of the nanowire structural element from FIG. 6.

Figure 8:
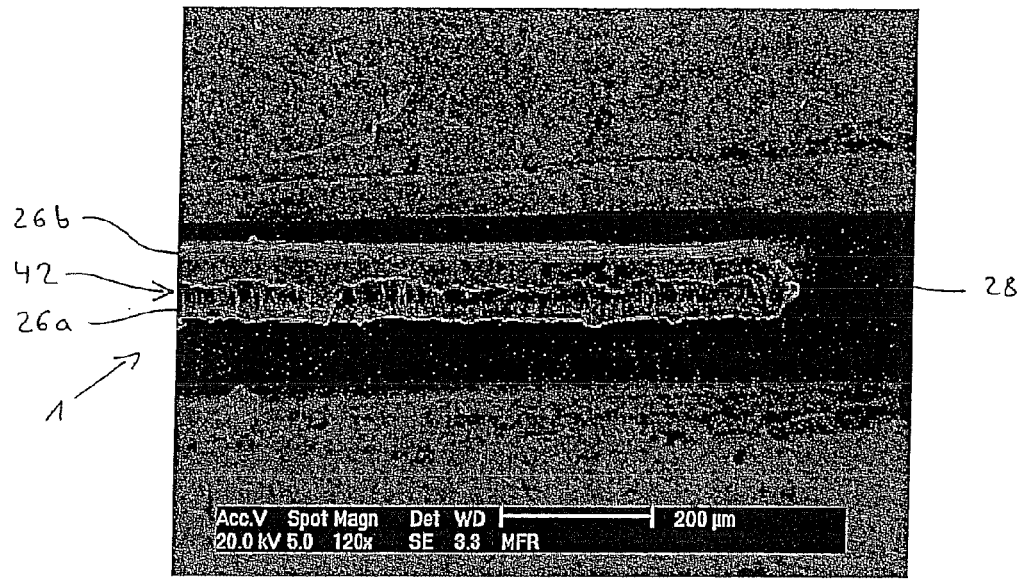

FIG. 8 An SEM image of a nanowire structural element open at two sides and closed at two sides with a nanowire array of platinum nanowires.

Figure 9:

FIG. 9 An enlarged SEM image of the nanowire array from FIG. 8.

Figure 10:
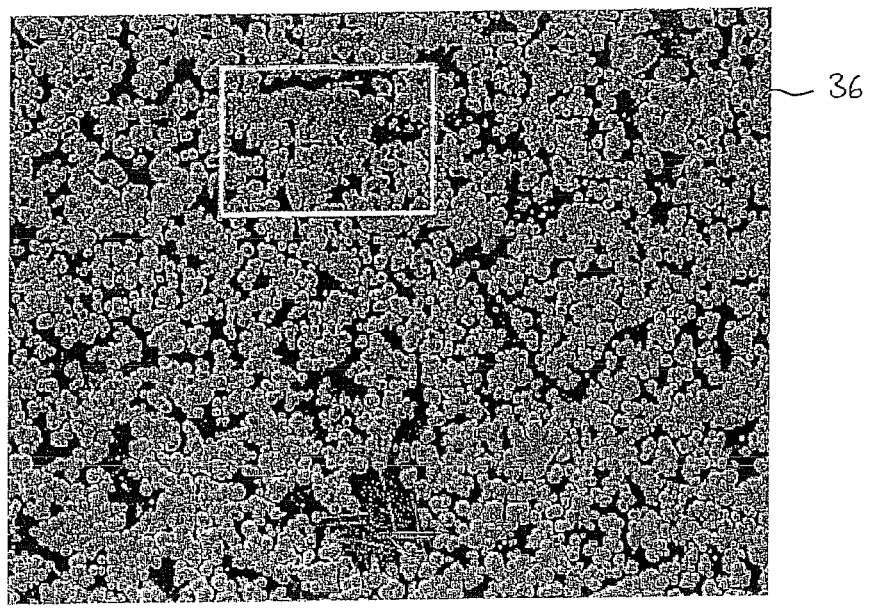

FIG. 10 An SEM image (edge length approx. 350 µm) of a platinum nanowire array subjected to direct current deposition with caps of different sizes.

Figure 11:
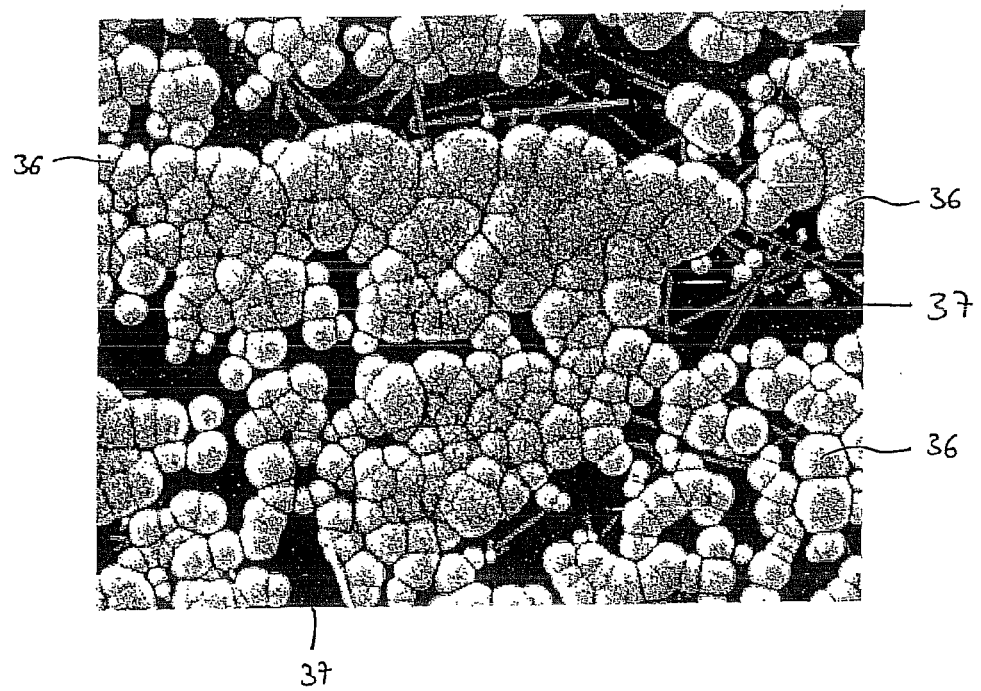

FIG. 11 An enlarged detail from FIG. 10 (edge length approx. 100 µm).

Figure 12:
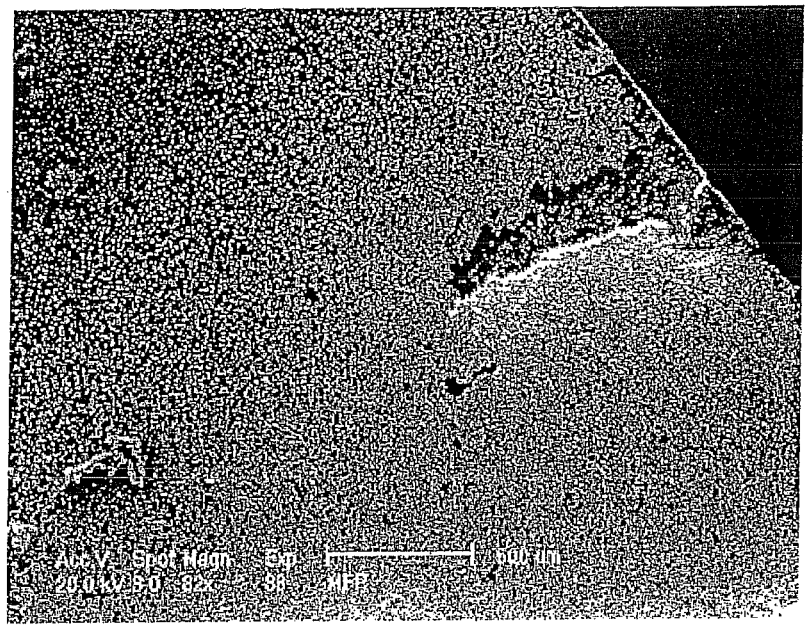

FIG. 12 An SEM image of a Pt nanowire array subjected to direct current deposition, wherein the spatial distribution of the caps is shown and showing the locally contained development of caps.

Figure 13:
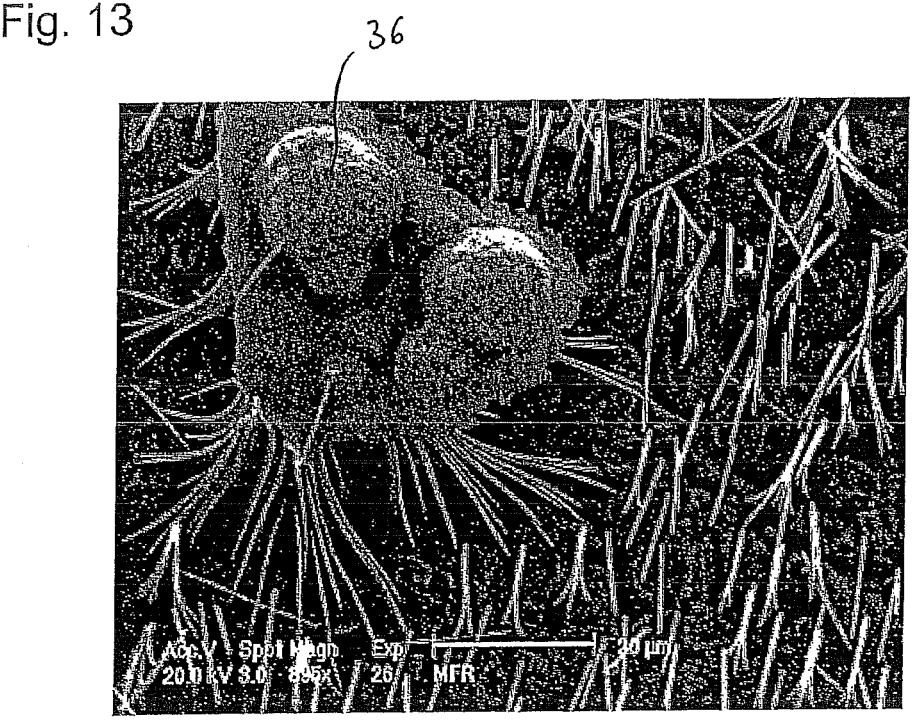

FIG. 13 A cut-away enlargement of the image from FIG. 12.

Figure 14:
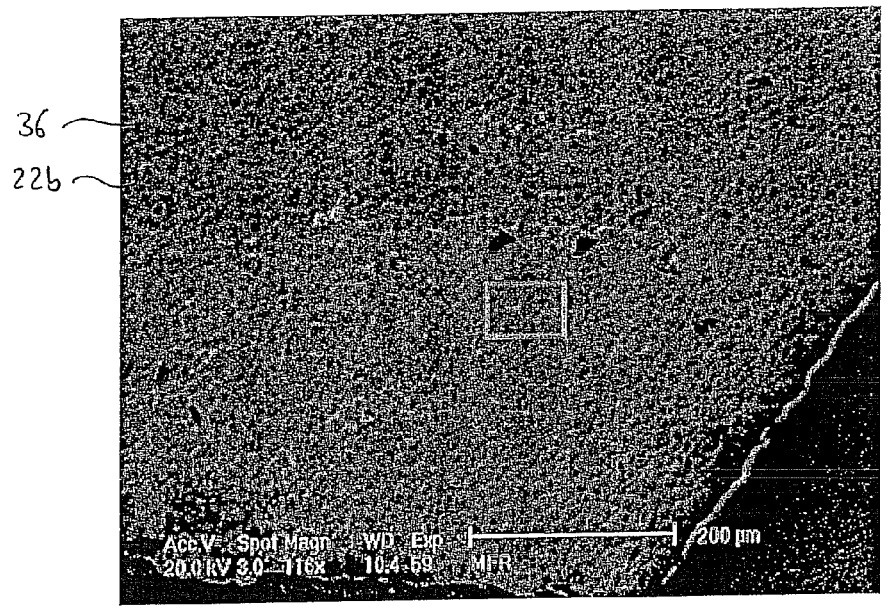

FIG. 14 An SEM image of a Pt nanowire array subjected to reversed pulse deposition with caps merged together to form a closed layer.

Figure 15:
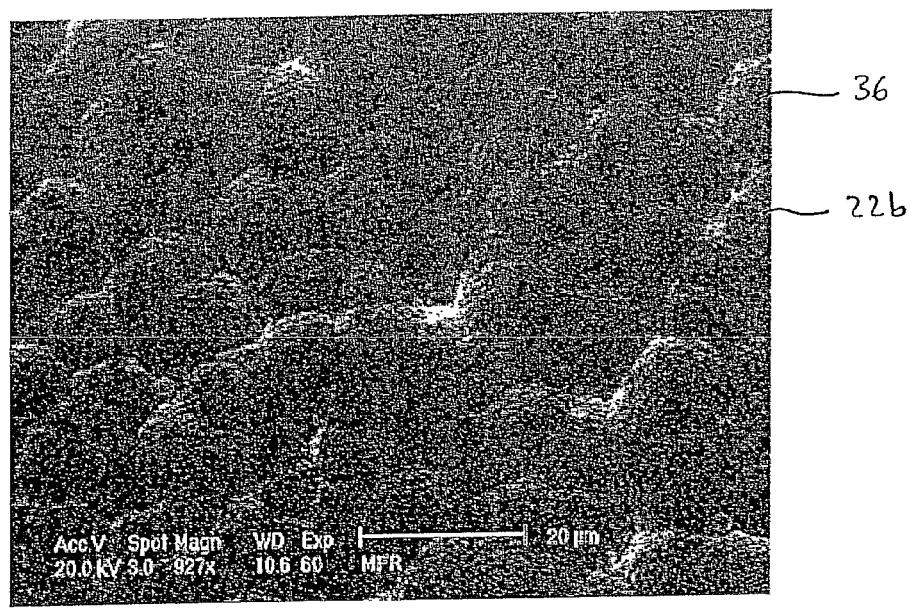

FIG. 15 An enlarged detail from FIG. 14.

Figure 16:
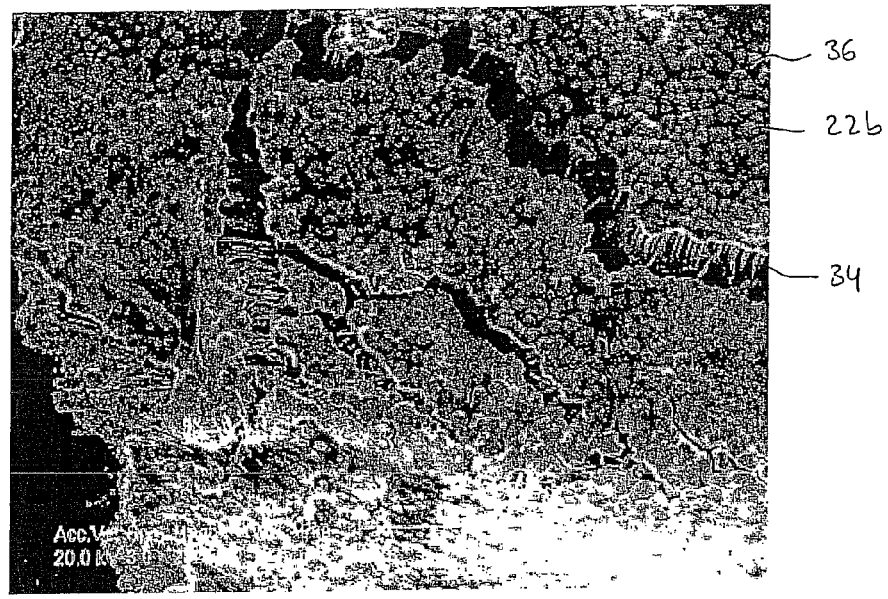

FIG. 16 An SEM image of a Pt nanowire array exposed to a mechanical load.

Figure 17:

FIG. 17 An enlargement of a detail from FIG. 16.

Figure 18:
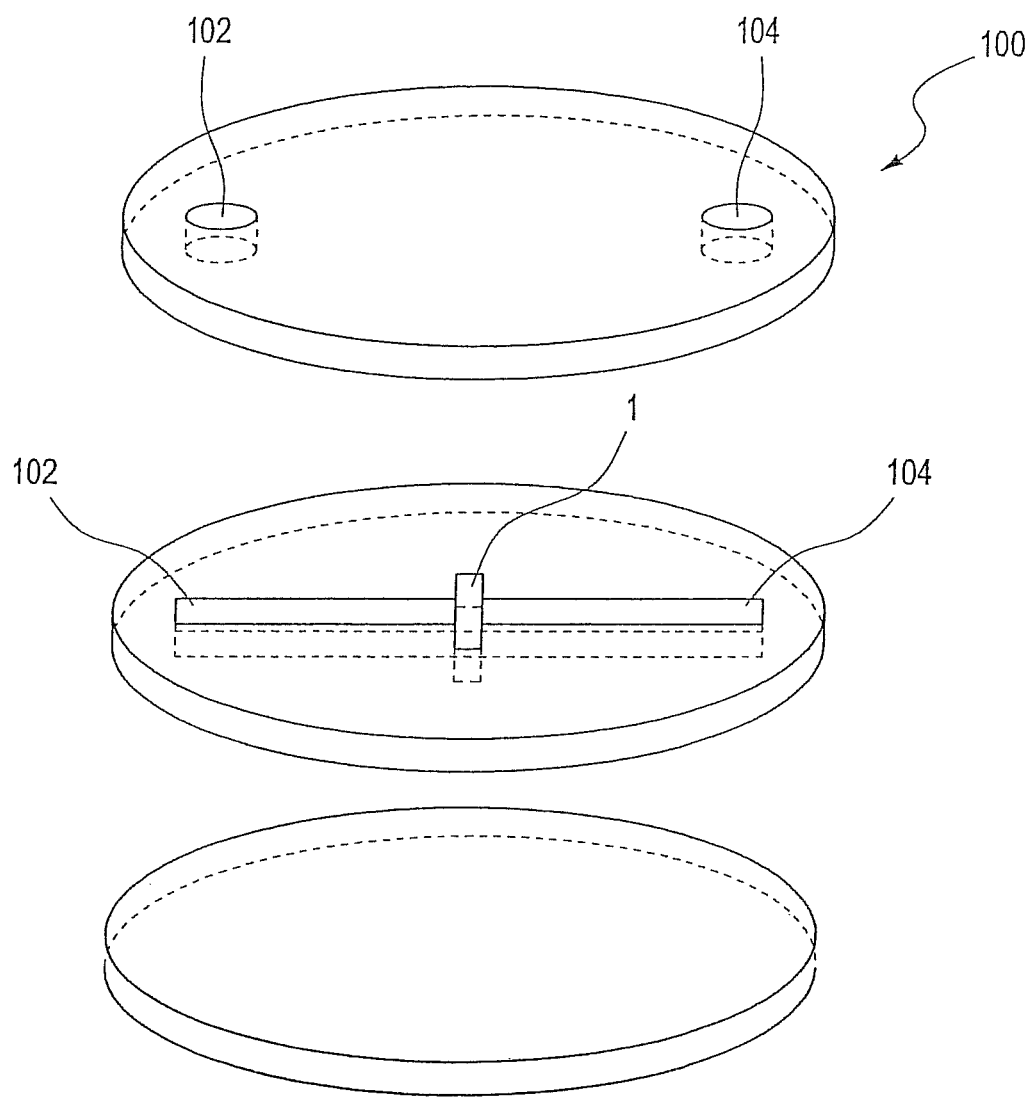

FIG. 18 A schematic exploded view of a microreactor with the nanowire structural element for flow-through operation.

FIG. 19 An enlargement of a detail of a perforated mask.

FIG. 20 An enlargement of a detail of an opening in the perforated mask from FIG. 19

FIG. 21 An overview of the production of numerous island-like microelement nanowire structural elements using a perforated mask.

Figure 22:
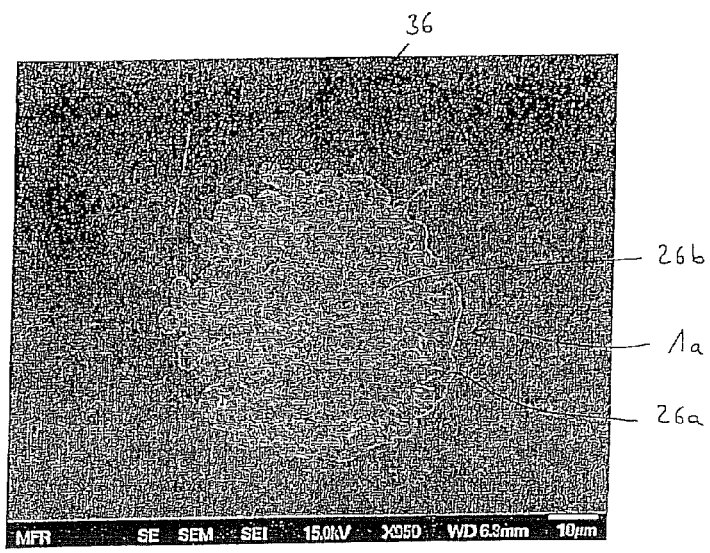

FIG. 22 An SEM image of a microelement nanowire structural element with a view of one of the two cover layers.

Figure 23:
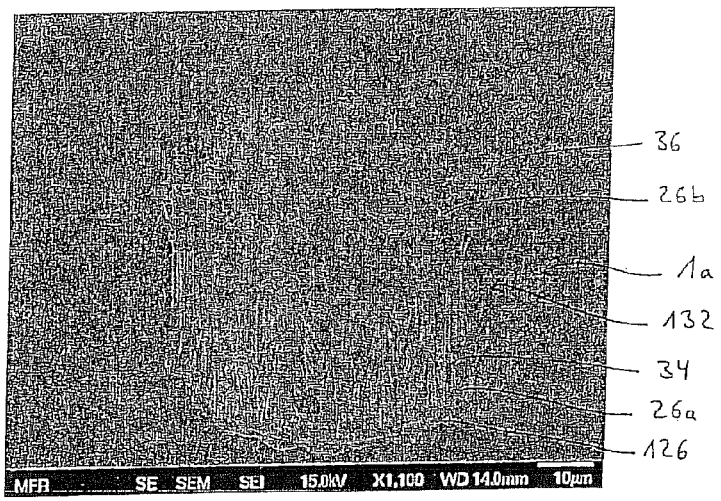

FIG. 23 Another SEM image of the microelement nanowire structural element from FIG. 22 with a diagonal view of the extent of the microelement nanowire structural element.

Figure 24:
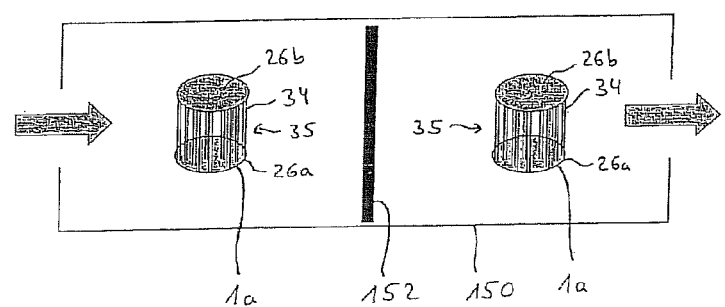

FIG. 24 A schematic presentation of a sensor element with two microelement nanowire structural elements.

DETAILED DESCRIPTION OF THE INVENTION

Overview of the Production Process

The production of nanowire structural elements is based on a template based process. The partial steps of the process are schematically presented in FIG. 1. For purposes of clarity, the letters correspond to the above mentioned process steps, which ideally are carried out in the order shown in FIG. 1, i.e. (c1), (b), (c2), (d1), (d2), (e). It is, however, basically possible to use a different sequence, such as, to etch from two sides and subsequently to then first to apply the cathode layer partial step ((c2) before (b)).

In accordance with FIG. 1, first a template foil 12 is bombarded with ions 14, wherein latent ion tracks 16 are generated in the substance of the template foil 12 along the trajectory (c1). The template foil 12 is a polymer foil in this example, specifically, a polycarbonate foil.

Subsequently, on the first side 12a of the template foil 12, a thin, conductive metallic layer 22a, e.g. gold, is sputtered onto said, forming a first partial layer.

Subsequently, the first partial layer 22a is reinforced electrochemically with a second partial layer 24a thus forming the first cover layer 26a, which later serves as a cathode for nanowire deposition (b). For the electrochemical deposition of the second partial layer 24a, the template foil 12 is mounted in the deposition device 82 shown in FIGS. 3-5.

Subsequently, the template foil 12 coated on one side is then removed from the deposition device 82, and the latent ion tracks 16 are chemically etched, wherein uniform nanopores 32 are created. Alternatively, the etching process may also be carried out in the deposition device 82, in that the etching solution is placed in the appropriate cell 88, and after completion of the etching, removed from said. A removal of the template foil and the replacement of said are not necessary. The diameter of the nanopores 32 can be controlled by controlling the etching time period (c2).

Following this, the template foil 12 prepared in this manner is placed again in the deposition device 82, and using the appropriate electrochemical process, the desired metal is depositioned in the nanopores 32 (d1). When the nanowires 34 reach the ends of the pores 32b at the second side 12b of the template foil 12, caps 36 begin to form. Under suitable conditions, the caps 36 merge together in a layer, forming a second, closed, but not yet sufficiently stable, metallic layer 22b parallel to the first cover layer or cathode layer (d2). This metallic layer, in this example, is a first partial layer 22b, on which a second metallic layer is depositioned, forming a second partial layer 24b (d2). By means of the second partial layer 24b, the caps which have merged together are embedded in a mechanically stable manner. In this way, the first and second partial layers 22b, 24b together form the second cover layer 26b.

Finally, the polymer foil 12 is dissolved in an organic solvent suited to this purpose (e). The nanowire structural element 1 produced hereby in accordance with the invention is shown in FIG. 2. At least the inner side facing the hollow chamber-like structure 42 of the second cover layer 26b is at least partially formed hereby by means of an electrochemically depositioned layer 22b.

The template based method has the advantage that many of the parameters can be specifically manipulated. The length of the nanowires 34 is determined by the thickness of the template 12 used and ideally is 10-100 µm, particularly preferred is circa 30 µm±50%. The surface density of the nanowires 34 is determined by the irradiation and for production of the array is ideally between $1 \times 10^7$ and $1 \times 10^9$ cm$^{-2}$. The diameter D of the nanowires 34 is determined by the time period of the etching and may be from ca. 20 nm to 2000 nm. The aspect ratio may have values of up to 1000.

The thickness of the two cover layers 26a, 26b is controlled through the time period of the respective electrochemical deposition, and should be thick enough that sufficient stability is obtained. Ideally, it is from ca. 5 µm to 10 µm.

Possible materials for the nanowires are metals which are suited to electrochemical deposition. Experience has been made with the following metals: Cu, Au, Bi, Pt, Ag, Cu, Cu/Co multilayer, $Bi_2Te_3$.

On the one hand a large number of nanowires 34 with small diameters D is desired, in order to obtain a large active surface area, and on the other hand a good mechanical stability should be obtained. The optimization of this depends on the material used and is adjusted to the needs accordingly.

For nanowire structural elements 1 with platinum nanowires 34 between copper partial layers 24a, 24b, a stable construction is produced with $10^8$ wires per $cm^2$ having a diameter of 250 nm and a length of 30 µm. The aspect ratio here is 120. Such elements are suited, for example, for use as catalytic elements.

To produce the nanowire structural elements 1, as an alternative to polymer foils 12, other template foils such as hard template foils of aluminum oxide may also be implemented. The pore diameters which can be achieved here are between 10 and 200 nm. The density hereby is sufficient at ca. $6.5 \times 10^8$-$1.3 \times 10^{11}$ $cm^{-2}$. Porous aluminum oxide templates allow for the generation of uniformly arranged structures. It is also conceivable to use templates of ion track etched glasses and mica-films. With these templates, the removal of the template is achieved with hydrofluoric acid (HF), wherein the selection of the metal for the wire deposition and the metallic layers is somewhat limited.

Example 1

For the production of a nanowire structural element 1, a circular shaped (r=1.5 cm) polycarbonate foil 12 (Macrofol®) irradiated with heavy ions 14 having an energy of 11.1 MeV/u and a fluence of $3 \times 10^7$ ions/$cm^2$ is used. Prior to the application of the conductive metallic layer 22a, each side of the polymer foil 12 is irradiated for one hour with UV light, in order to increase the selectivity of the etching along the tracks 16.

A gold layer 22a is sputtered onto the first side 12a of the polymer foil 12, having a thickness of ca. 30 nm. This is reinforced by a potentiostatic deposition of copper from a $CuSO_4$ based electrolyte solution (Cupatierbad, Riedel) with a voltage of U=-500 mV, wherein a copper rod electrode serves as the anode (partial step 24a). The deposition is stopped after 30 minutes, at which point the copper layer 24a is approx. 10 µm thick. Subsequently, etching is carried out from the untreated side 12b of the template foil 12 at 60° C. with an NaOH solution (6 M) for 25 minutes and thoroughly rinsed with deionized water, to remove residual etching solution. At this point, the nanoporous template foil 12 is mounted in the deposition device 82.

The deposition of nanowires 34 is carried out at 65° C. with alkaline Pt electrolytes (Pt—OH bath, Metakem). To generate the nanowires 34 and the caps 36, the process of the reversed pulse deposition is used in order to compensate for the slow diffusion driven transportation in the nanopores 32, and to obtain uniform development of nanowires 34 and caps 36. Following a deposition pulse of U=-1.3 V for 4 seconds, there is an anodic pulse for 1 second at U=+0.4 V. After ca. 80 minutes, the deposition is stopped, and the development is checked. The caps 36 at this point are sufficiently merged for a partial cover 22b, such that subsequently the potentiostatic deposition of a copper partial cover 24b at U=-500 V for ca. 30 minutes can be carried out.

Finally, the template foil is removed, wherein the entire nanowire structural element with the template foil 12 is placed in a container with 10 ml dichloromethane for several hours. The solvent is replaced three times in order to fully remove residual polymers from the interior 38 of the structure which is enclosed on both sides by the cover layers. The hollow chamber-like structure 42 between the cover layers 26a, 26b with the nanowire array 35 can be seen in a scanning electron microscope (SEM) image in FIGS. 6 and 7. The nanowires 34 here have a diameter of approx. 650 nm.

Example 2

In reference to FIGS. 8 and 9, a further embodiment is presented, to show, among other points, that the parameter diameter and number of nanowires 31 can be varied. The etching period of 18 minutes results in nanowires 34 having a diameter of ca. 250 nm. The surface density (number per unit of surface area) is $10^8$ $cm^{-2}$. For electrochemical deposition of the wires, the reversed pulse method is again used. A deposition pulse of $U_1$=-1.4 V for 40 ms is followed by a shorter counter pulse of $U_2$=-0.1 V for 2 ms and a pulse interval of 100 ms with a voltage of U=-0.4 V, which corresponds to an excess voltage of ca. 0 V. I.e., during the counter pulse, the system is in a state of equilibrium.

The nanowire array 35 is cut to a rectangular nanowire structural element 1. Subsequently, a copper layer is potentiostatically depositioned onto the entire nanowire structural element again with a template foil 12, in order that it is also closed on all sides. Following this, the two short ends are cut and the template 12 is then removed in order to obtain a nanowire structural element 1 which is open on two opposing ends and sealed on the other two opposing edges. It is important to realize that the edge 28 shown at the right in FIGS. 8 and 9 is sealed in a water tight manner, in that the upper cover layer 26b is extended over the edge 28. This nanowire structural element 1 is suited ideally for use as a catalytic element for conducting a fluid which is to be catalyzed, which can be introduced at one of the open ends and expelled at the opposite open end.

Construction for the Electrochemical Deposition

With reference again to the FIGS. 3-5 the electrochemical deposition of the nanowire array 35 consisting of numerous nanowires 34 is carried out using the deposition device 82 which shown in FIG. 3 in its entirety. It consists of a metal housing 84, in which the metal sled containing one of the two electrolysis cells 86, 88 can be inserted. Due to the good heat transfer properties of metal, it is possible to temper the deposition device by controlled external heating.

The electrolysis cells 86, 88 made of PCTFE have on their two facing sides, in each case, circular openings 87, 89 of the same size and can be pressed together firmly with a hand turned screw. A copper ring 92 between the two electrolysis cells 86, 88 serves as a cathode, or respectively, to establish contact with the first cover layer for the electrochemical deposition.

With reference to FIG. 4, for electrochemical reinforcement of the partial layer 22a, the ion track etched template foil 12 is mounted between the two electrolysis cells 86, 88 such that the partial layer 22a, in this case, the sputtered gold layer 22a, makes good contact with the ring shaped copper electrode 92. On both sides of the copper ring being used as a cathode, electrolytes are injected into the electrolysis cells.

The electrochemical reinforcement of the gold layer 22a on the first cover layer 26a is carried out with a first anode 94, which is placed in the electrolysis cell 86 facing the partial layer 22a, and an external power source with a control device.

After removing the template foil 12 and etching the nanopores 32 outside of the deposition device 82, the template foil 12 is placed again in the deposition device 82.

With reference to FIG. 5, the template foil 12 which has been coated on one side and made porous is again placed in the deposition device 82 as in FIG. 4 for electrochemical deposition of the nanowires 34, the caps 36 and, where applicable, the completion of the second cover layer 26b, such that the first cover layer 26a makes contact with the ring electrode 92. At this point, deposition is carried out on the second side 12b of the template foil 12 with a second anode 96 located in the electrolysis cell 88 on the side away from the first cover layer 26a.

Examination of the Influence of the Electrochemical Deposition Conditions to the Development of the Nanowires and Caps With the pulsed deposition procedure for generating nanowires 34, a uniform length of the nanowires can be advantageously obtained at any point in time of the deposition. This can be explained, without claim to completeness and accuracy, in that the diffusion layers are kept relatively short in comparison to direct current deposition. In the intervals (equilibrium or counter pulse) between the deposition pulses, metal ions can re-diffuse such that on the entire electrode surface a nearly uniform concentration is obtained at the beginning of each deposition pulse, which results in a homogenous development. The diffusion layers barely overlap each other and irregularities in the surface are not enhanced.

It has been determined that the pulsed deposition procedure ensures a size distribution of the caps 36 and it is therefore advantageous to implement the pulsed deposition procedure at least for the production of the caps.

In order to examine the development of the caps, experiments using direct current deposition and reversed pulse deposition were carried out and compared.

Deposition with Direct Current

FIGS. 10 and 11 show a nanowire array formed using direct current after the formation of the caps 36. This means that the production process is interrupted after the formation of the caps 36 and the template foil 12 is removed before formation of the complete second cover layer 26b in order to more exactly study development of the caps. If the enlargement is not to large, the caps 36 seem to be more or less homogenous in their size distribution (FIG. 10). It may be clearly seen however that the caps 36 are partially merged but there are a few larger gaps 37 between them. Furthermore, a few isolated caps 36 can be distinguished.

This becomes clearer in the enlargement in FIG. 11, which furthermore gives an impression of the size distribution. The caps demonstrate both a strong fluctuation in their spatial distribution as well as in their connectivity to other caps 36.

FIG. 12 shows a large surface of a nanowire array which was produced using direct current for the purpose of studying said, after removal of the template foil 12 before generating the complete second cover layer 26b. It is possible to see that the development of the caps 36 is dependent on their position in the array.

With reference to the enlarged presentation in FIG. 13, the spatial distribution of the caps is not homogenous. In particular, single isolated caps 36, surrounded by numerous wires which do not show even the beginnings of caps, can be observed.

Without claim to completeness and accuracy, the main cause for the unevenness of the size distribution is seen to be the overlapping of the diffusion layers of individual nanoelectrodes which may be treated as nanowires. If the nanowires 34 are still deep in the nanopores 32, the metal ions must travel a long distance through the planar diffusion. The longer the nanowires 34 grow, the higher they climb into the pores 32 and come closer to the end of the pore 32b, where the development of the caps 36 begins. In connection with this, the diffusion layer extends further into the solution and the probability of overlapping other layers increases. In addition, it must be taken into consideration that the diffusion deviates from planar behavior as the development progresses, and in the end can be seen as completely hemispherical, as soon as the length of the nanowires 34 corresponds to the thickness of the polymer foil 12.

Nanoelectrodes which are fairly close to others compete for metal ions in the solution and as a result develop more slowly than electrodes which are relatively isolated. The unevenness of the size distribution, accordingly, is a direct result of the randomness wherein the pores 32 are arranged.

Presumably the differences in the development rates assume greater importance as soon as planar and hemispherical diffusion occur in the same area. This is the case when a nanowire 34 has achieved the end of the pore 32b and begins to form a cap 36, while the wires 34 in the direct surroundings are still in the pores 32 where they are subjected to planar diffusion. Due to the naturally uneven surface of the polymer foil 12, the pores 32 have different sizes from the beginning, wherein the nanowires 34, when growing at the same rate will reach the ends of said pores at different times.

The possibility that nanowire arrays with caps generated using direct current for the production of a stable nanowire structural element 1 may be used has not been eliminated. Accordingly, further tests using pulsed deposition have been carried out in order to study the development of caps using this process.

Reversed Pulse Deposition

In the FIGS. 14 and 15 a platinum nanowire array 35 produced with reversed pulse deposition is shown. The caps 36 have merged to form a dense, closed layer 22b made possible due to a better size distribution, which is the aim of the reversed pulse deposition. The layer 22b is homogenous throughout the entire electrode surface and has no gaps. It should be noted that with this test as well, after the formation of the metal layer 22b consisting of the fully merged caps 36, the deposition procedure of the second cover layer 26b is not yet fully carried out, and thus the second cover layer 26b is not yet completely formed, but rather the metal layer 22b consisting of the merged caps 36 represents only a partial layer 22b of the second cover layer 26b.

Should this incomplete array be exposed to a mechanical load in that, for example, it were to be squeezed with a forceps, the layer 22b formed by the merged caps 36 would tear, as is shown in FIG. 16, allowing for a view between the metal cover layers into the interior of the array. FIG. 17 shows a cut-away enlargement of a tear. It can be clearly seen that the parallel nanowires 34 hold the metal layers, with which they are integrally joined, at a uniform distance from each other.

The advantageously narrower size distribution of the caps 36 in comparison to those produced with direct current deposition can be explained, without claim to completeness and accuracy, by the shorter diffusion layer. In the intervals between pulses, metal ions can re-diffuse, and as a result, on the entire surface of the electrode a nearly uniform level of concentration at the beginning of each deposition pulse is obtained, which results in a homogenous development. The diffusion layers hardly overlap each other and irregularities in the surface are not enhanced.

In summary, it may be determined that the pulsed deposition of the nanowires 34 and the caps 36, particularly when using reversed pulse deposition, allows for an excellent uniformity in development of the caps. In this case, the electrochemical deposition for the generation of the nanowires 34 is carried out at least until the caps 36 have formed on the nanowires, and said have merged to form a surface covering layer 22b. Subsequently, either an additional deposition of electrochemical material is carried out in order to reinforce the layer 22b comprised of merged caps 36 to the point where the stable second cover layer 26b is generated, or, in a separate deposition procedure a second partial layer 24b is created in which the merged caps 36 are embedded. For the production of the stable nanowire structural element 1 according to the invention, the template foil 12 is removed specifically after this step has first been completed. The thickness of the second cover layer 26b should be at least 1 µm. However, the thickness is preferably greater than 5 µm, e.g. between 5 µm and 10 µm. The same applies to the first cover layer 26a.

Structural Characteristics of the Nanowires

In the framework of the invention the structural characteristics of the nanowires 34 made of different materials is also studied. With electrochemically depositioned material it is possible, for example, to control the size of the crystallite. This affects the mechanical stability, the thermal and electrical transference characteristics as well as the surface area and thereby also the catalytic activity. Many characteristics can thereby be strategically influenced.

In particular, the structure of the nanowires 34 is studied using X-ray diffraction. For this, the texture as a function of the electrochemical deposition is analyzed.

Pt nanowires 34 produced using direct current show a clear <100> texture. The texture coefficient $TC_{100}$ is 2.32, wherein the maximum value is 3. The size of the crystallite is determined by the half-width of the platinum signal by means of the Scherrer equation, and is 8 nm. For catalytic application, the smallest possible crystallite is desired. The value given here lies in the range of the nanoparticles otherwise used for catalysis. Based on this it may be assumed that the crystallite size can be reduced even more through modification of the electrochemical deposition conditions.

When studying nanowires 34 which are produced using pulsed deposition, one finds no specific texture. The intensity of the signals corresponds to those of polycrystalline platinum.

Finally, a sample produced using reversed pulse deposition, is studied. This also shows a clear <100> texture, wherein the texture coefficient $TC_{100}$ is 4.6. The crystallites display accordingly a preferred orientation, wherein the degree of the alignment is 83%. An alignment of at least 50% in this case is advantageous.

The characterization by means of X-ray diffraction of nanowires 34 produced using different means has shown that the deposition conditions have an effect on the texture. Therefore, the structure of the nanowire can be strategically influenced. It is expected that even single crystalline nanowires can be produced when the surplus voltage is selected at a correspondingly low level.

The surface of a nanowire 34 does not correspond to smooth surface of a cylinder, which is the basis for the calculation of the geometrical surface, but rather, it displays numerous recesses and swellings in its contour which significantly increases the surface area. The actual size of the surface area is therefore typically larger than the geometrical surface area, because, among other reasons, the crystallites from which the nanowires 34 are constructed are very small. In order to obtain a more precise idea of the surface area of the nanowire arrays 35, cyclovoltammetric measurements at 60° C. in 0.5 M $H_2SO_4$ are carried out for a potential range of 0-1,300 mV with a standard hydrogen electrode. From the load in which the adsorption of hydrogen is transmitted, it is possible, taking into account the capacitive currents, to calculate the surface area of the electrodes. The cyclovoltammetric examination of nanowire arrays shows that the actual surface area is greater than the geometrical surface area by a factor ranging from 4-5.

Applications

As a catalyzes it is possible to connect a series of numerous nanowire structural elements 1 according to the invention. Based on measurements, the nanowire structural element 1 is suited individually for application in microstructured systems having three-dimensional structures wherein the internal measurement is less than 1 mm and for the most part lies between ten and a few hundred micrometers.

FIG. 18 is a schematic illustration of a microcatalyzer 100, in which a nanowire structural element 1 according to the invention is placed between a fluid intake 102 and a fluid discharge 104. It is conceivable that in a microcatalyzer 100 of this sort gas or fluid phase reactions can be carried out. For this purpose, a gas or fluid flow is directed under pressure through the microcatalyzer 100.

The nanowire structural element 1 produced according to the invention furthermore inherently contains an electric contact to all of the nanowires located between the two metal layers. As a result, a controlled voltage may be applied to the nanowires 34 thereby enabling Electrocatalytic processes. Furthermore, the component may be used as an amperometric sensor.

Production of Microelements Using a Radiation Mask

In accordance with the invention, it is possible to create nanowire structural elements or nanowire arrays of very small sizes enclosed at both sides by the two cover layers 26a, 26b, in that the template foil 12, a polymer foil in this example, is irradiated with heavy ions through a corresponding mask 110 (step (c1) in FIG. 21). The mask 110, e.g. a perforated mask, which is already applied in step (c0) contains numerous openings 112 or perforations, wherein each opening 112 defines a future microelement 1a. The mask 110 covers the template foil 12 during the irradiation, and latent ion tracks 16 are formed thereby, which are subsequently etched to form nanopores 32 in the areas which are not covered by the mask, i.e. at the openings 112 of the mask 110. The layout and the shape of the microelement 1a are determined therefore by the mask 110.

This process is specifically for the production of many very small nanowire structural elements, as stated, in the form of microelements 1a. The microelements 1a which may be produced in this manner consist of two cover layers, integrally joined to the nanowires, which may have a diameter of less than 500 µm, and particularly less than 100 µm, and where applicable, even less, to a size of only a few micrometers. The diameter refers to the size measured on a plane parallel to the cover layers 26a, 26b or perpendicular to the nanowires 34. For this, for example, the aspect ratio of the diameter of the microelement to the thickness of the microelement may be less than 20:1 or 5:1. The thickness of the microelement refers to the measurement perpendicular to the plane of the cover layers 26a, 26b (approximately the distance separating the two cover layers).

FIG. 19 shows a detail of an exemplary perforated mask 110 and FIG. 20 shows an enlargement of a perforation 112.

The perforations 112 of the perforated mask 110 in this example have a diameter of 50 μm, such that only nanowires 34 having a diameter of around 50 μm can be electrochemically depositioned, thereby allowing for the production of microelements 1a having a diameter of approximately 50 μm.

The FIGS. 22 and 23 show one of the many microelements 1a produced using the perforated mask 110 having a diameter of approximately 50 μm and a thickness of approximately 30 μm. The microelement 1a has cover layers 26a, 26b sealed on both sides, which are integrally joined to nanowires 34. The sealed metal layers 26a, 26b, comprised of merged caps 36, 126 which have formed on both sides 12a, 12b of the template foil 12, display a minimally larger fluctuation than the nanowire array 35a in the interior. The irradiation is carried out with $10^8$ ions per $cm^2$. Accordingly, there are approximately 2,000 nanowires located between the metal layers 26a, 26b of the 50 μm microelement 1a.

In this example, the perforated mask 110 for the ion irradiation has approximately 2,000 perforations 112 on the entire deposition surface of approximately 0.5 $cm^2$, such that approximately 2,000 microelements 1a with nanowire arrays 35a in islands 116 in the template foil 12 can be created at once.

This production of many microelements 1a with nanowire arrays 35a in a template foil 12 is more labor intensive than the production of a nanowire array 35 over an entire deposition surface because additional steps must be carried out.

Prior to the etching of the latent ion tracks 16 into nanopores 32, a metallic initial layer 25 is applied to the first side 12a of the template foil 12. The initial layer 25 serves in turn as a temporary cathode layer for the deposition of the nanowires 34. This initial layer 25 is removed after the caps 36 have formed on the second side 12b of the template foil 12 opposite the initial layer 25, in order that the microelements 1a can later be separated. A selective removal is possible, in particular, when the initial layer 25 is comprised of a different electroconductive material, in particular, a metal other than that from which the nanowires 34 are made.

Furthermore, the caps 36 which are formed first, those on the second side 12b of the template foil 12, using a selectively removable conductive layer, also preferably a metallic layer, are extended, forming a second temporary cathode layer 118 for further deposition. By means of the second cathode layer 118, the nanowires 34 of the numerous island-like distributed microelements 1a are in contact electrically with the caps 36 on the second side 12b, and it is now possible to form second caps 126 on the nanowires 34 on the first side 12a of the template foil 12, on which the initial layer 25 is located. When a—sufficiently stable—metal layer of merged second caps 126 has formed over the nanowires 34, the second temporary cathode layer 118 on the second side 12b can be removed. Subsequently, the template foil 12, a polymer matrix in this example, is dissolved and individual microelement nanowire structural elements 1a are left having the size of the perforated mask 112 with cover layers 26a, 26b on each side, consisting of merged caps in each case. An example of a microelement nanowire structural element 1a produced in this manner is shown in FIGS. 22 and 23, wherein in a single processing, as described above, numerous microelement nanowire structural elements 1a are produced.

Through the use of masks 110 for irradiation there is the advantage that the microelements 1a with nanowire arrays 35a produced can be used directly for integration, without further processing. The nanowire arrays 35a of the microelements 1a are open celled along the perimeter 132 in the plane parallel to the cover layers 26a, 26b, wherein the open cell characteristic is already generated in the deposition, such that an uncut microelement 1a with a nanowire array 35a is generated on all sides along the perimeter 132. Mechanical loads, such as resulting from cutting the sides or edges 134 can in this manner be avoided. In FIGS. 22 and 23 it may be seen that the cover layers 26a, 26b are formed of merged caps 126 or 36, and that these protrude somewhat at the edges. The edge is therefore formed by the naturally developed and merged caps. Here it is readily seen that the microelement nanowire structural element 1a is produced using this special process and in particular, that it is uncut at the edges.

Because all nanowires 34 have electrical contact at both ends, the microelement 1a with nanowire arrays 35a is suited for production of miniaturized sensors. Due to the large number of wires, not only a high sensitivity but also a defect tolerance should result.

FIG. 24 shows an example of a sensor 150, for measuring gas flow, temperature and use as a motion sensor, for example. The sensor 150 has at least one measuring device with a first and second microelement nanowire structural element 1a, wherein the microelement nanowire structural elements 1a in each case have cover layers 26a, 26b, wherein each of the two nanowire structural elements 1a have electrical contact through one or both of the two cover layers 26a, 26b, wherein the two nanowire structural elements 1a are contacted separately. A heating element is located between the two microelement nanowire structural elements, such as a microwire 152 which may be heated by means of applying voltage. The adjustment of the resistance of the sensor element 150 is used as a measure for the gas flow rate or the change in temperature, or change in position.

It is clear to the person skilled in the art that the preceding descriptions of embodiments are to be understood as exemplary, and that the invention is not limited to said, but rather, can be varied in numerous ways, without abandoning the scope of the invention. In particular, the production of a microcatalyzer is only one of many uses for the nanowire structural element of the invention. Furthermore, it is clear that the characteristics are, regardless of whether they are presented in the description, the claims, the illustrations or otherwise, also define significant components of the invention, even if they are described in conjunction with other characteristics.

The invention claimed is:

1. A nanowire structural element with a hollow chamber-like structure, which includes:
    an array of numerous nanowires standing next to each other, and
    two spaced cover layers,
    wherein the nanowires extend perpendicularly between the two cover layers and the nanowires are integrally joined at their first ends to the first cover layer and at their second ends to the second cover layer such that the nanowires firmly connect the two cover layers to each other and define the space between the two cover layers,
    wherein interconnected open spaces exist between the nanowires,
    such that a stable and freestanding sandwich-like nanostructure contained on two sides by cover layers and permeated with numerous nanowires in a column-manner and a two-dimensionally open cell hollow chamber-like structure is defined in the plane parallel to the cover layers in such a manner that between the two cover layers a fluid can be fed through the two-dimensional open cell hollow chamber-like structure,
    wherein the nanowires grow caps, wherein the caps have at least partially merged together with each other and the merged caps form a first partial layer of the second cover layer and wherein the second cover layer contains a second partial layer on top of the first partial layer formed by the caps which have merged together.

2. A nanowire structural element according to claim 1, wherein the nanowires are formed from electrochemically depositioned material.

3. A nanowire structural element according to claim 1, wherein the first of the two cover layers is formed by at least two layers.

4. A nanowire structural element according to claim 1, wherein the nanowires and at least a portion of the second cover layer form an, integrally formed unit.

5. A nanowire structural element according to claim 1, wherein the geometric specific surface of the nanowires per area of the nanowire structure element and per length of the nanowires is greater than or equal to 5 mm$^2$/(cm$^2$ μm).

6. A nanowire structural element according to claim 1, wherein the nanowires display a crystallite texture or a single crystal structure.

7. A nanowire structural elements according to claim 1, wherein on at least one end of the nanostructure element at least one of the two cover layers has been extended over the end and integrally joined to the other cover layer in such a manner that the end is closed.

8. A nanowire structural element with a hollow chamber-like structure containing:
an array consisting of numerous neighboring nanowires, and
two spaced cover layers,
wherein the nanowires extend perpendicularly between the two cover layers and the nanowires are integrally joined with their first ends to the first cover layer and with their second ends to the second cover layer, such that the nanowires firmly connect the two cover layers, and define the space between the two cover layer,
wherein interconnected open spaces exist between the nanowires
such that a stable and freestanding sandwich-like nanostructure contained on two sides by cover layers and permeated with numerous nanowires in a column-manner and a two-dimensionally open cell hollow chamber-like structure is defined in the plane parallel to the cover layers in such a manner that between the two cover layers a fluid can be fed through the two-dimensional open cell hollow chamber-like structure, and
wherein the nanowire structural element is constructed in the form of a microelement,
wherein the nanowires grow caps, wherein the caps have at least partially merged together with each other and the merged caps form a first partial layer of the second cover layer and wherein the second cover layer contains a second partial layer on top of the first partial layer formed by the caps which have merged together.

9. A nanowire structural element according to claim 8, wherein both cover layers are formed at least in part by caps on the nanowires which have merged together.

10. A nanowire structural element according to claim 8 or 9, which, uncut, in a plane parallel to the cover layers is open celled along the perimeter.

11. A microreactor system that includes:
a microstructured channel system with a fluid intake and a fluid discharge,
at least one nanowire structural element (1) in accordance with claim 1 as a reactor element between the fluid intake and the fluid discharge,
such that fluid from the fluid intake can be introduced to the hollow chamber-like structure (42) between the two cover layers (26a, 26b), fed through the open spaces between the nanowires (34) and discharged from the hollow chamber-like structure (42) through the discharge,
wherein the two-dimensional open cell hollow chamber-like structure (42) of the nanowire structural element (1) between the two cover layers (26a, 26b) forms the reaction volume and the cylindrical surfaces of the nanowires (34) form the active surface area with which the fluid within the hollow chamber-like structure (42) interacts during the flow-through period.

12. A catalyzer system, that includes:
a microstructured channel system with a fluid intake and a fluid discharge,
at least one nanowire structural element (1) in accordance with claim 1 as a catalyzer element between the fluid intake and the fluid discharge,
such that fluid from the fluid intake is introduced to the hollow chamber-like structure (42) between the two cover layers (26a, 26b), fed through the open spaces between the nanowires (34) and then discharged from the hollow chamber-like structure (42) through the discharge,
wherein the two-dimensional open cell hollow chamber-like structure (42) of the nanowire structural element (1) between the two cover layers (26a, 26b) forms the catalytic reaction volume and the cylindrical surfaces of the nanowires (34) form the catalytic active surface with which the fluid within the hollow chamber-like structure (42) interacts during the flow-through period.

13. A catalyzer system according to claim 12, wherein the nanowires (34) are structured massively such that the catalyzer element is a bulk catalyzer.

14. A sensor element (150), in particular for measuring gas flow, temperature or motion, containing.
at least a measuring device with a first nanowire structural element (1, 1a) and a second nanowire structural element (1, 1a) in accordance with claim 8, wherein the nanowire structural elements (1, 1a) in each case have cover layers (26a, 26b) integrally joined to the nanowires (34) which can on both sides form a contact to the respective nanowire structural element and wherein a heating element (152) is located between the nanowire structural elements.

* * * * *